United States Patent
Tanassi et al.

(10) Patent No.: US 8,075,134 B2
(45) Date of Patent: Dec. 13, 2011

(54) METHOD TO REPRESENT IMAGES FOR DISSOCIATIVE STEREOSCOPIC VISION AND RELATED SYSTEM

(76) Inventors: Cesare Tanassi, Ponte Della Priula (IT); Walter Zanette, San Fior (IT); Irene Mogentale, Lendinara (IT); Gianluigi Meneghini, Selvazzano Dentro (IT)

(*) Notice: Subject to any disclaimer, the term of this patent is extended or adjusted under 35 U.S.C. 154(b) by 0 days.

(21) Appl. No.: 12/532,619

(22) PCT Filed: Mar. 11, 2008

(86) PCT No.: PCT/IT2008/000157
§ 371 (c)(1),
(2), (4) Date: Sep. 22, 2009

(87) PCT Pub. No.: WO2008/114298
PCT Pub. Date: Sep. 25, 2008

(65) Prior Publication Data
US 2010/0053551 A1    Mar. 4, 2010

(30) Foreign Application Priority Data
Mar. 22, 2007   (IT) .............................. MI2007A0578

(51) Int. Cl.
*A61B 3/08*   (2006.01)
*A61B 3/10*   (2006.01)
*A61B 3/14*   (2006.01)
*A61B 3/00*   (2006.01)

(52) U.S. Cl. ......... 351/201; 351/210; 351/205; 351/246
(58) Field of Classification Search ................. 351/201, 351/200, 205, 210, 246; 348/42, 43, 46, 348/51, 54, 55; 359/462, 464, 465, 466, 359/472
See application file for complete search history.

(56) References Cited

U.S. PATENT DOCUMENTS
| | | | | |
|---|---|---|---|---|
| 5,050,961 | A | * | 9/1991 | Venolia ......................... 359/465 |
| 2003/0048354 | A1 | * | 3/2003 | Takemoto et al. ............... 348/51 |
| 2006/0044388 | A1 | * | 3/2006 | Kim et al. ........................ 348/42 |

FOREIGN PATENT DOCUMENTS
| | | |
|---|---|---|
| EP | 1 489 858 | 12/2004 |
| EP | 1 662 808 | 5/2006 |

OTHER PUBLICATIONS
International Search Report for PCT/IT2008/000157, mailed on Sep. 26, 2008, 2 pages.

* cited by examiner

*Primary Examiner* — Mohammed Hasan
(74) *Attorney, Agent, or Firm* — Levine Bagade Han LLP

(57) ABSTRACT

The following is a method to represent images for dissociative stereoscopic vision, which allows, by means of some simple operations on stereoscopic images, to develop a device comprising a processing card and LCD shuttering goggles, which together with a computer equipped with a graphic card with LVDS output and any image display device, enable to perform visual acuity tests on patients.

4 Claims, 1 Drawing Sheet

METHOD TO REPRESENT IMAGES FOR DISSOCIATIVE STEREOSCOPIC VISION AND RELATED SYSTEM

CROSS-REFERENCE TO RELATED APPLICATIONS

This application is a U.S. National Phase of International Application No. PCT/IT2008/000157 filed Mar. 11, 2008, which claims priority to Italian Patent Application MI2007A000578 filed Mar. 22, 2007, the disclosures of which are incorporated herein by reference in their entirety.

FIELD OF THE INVENTION

This invention refers to a method to represent images for dissociative stereoscopic vision and related system.

BACKGROUND OF THE INVENTION

During optical and ophthalmological examinations, in order to explore specific functions of the visual apparatus, including stereoscopic vision, the patient needs to be shown different stimuli for each eye in binocular vision. The present systems use polarized or coloured filters. These are physically made up of two sheets. Two differently polarized filters (vertical and horizontal polarization) are placed side by side on the display surface, so that each filter covers half of it. The patient wears goggles, whose right lens has the same polarization as the filter covering the right portion of the screen, and the same goes for the left lens, so that each eye can only see the corresponding portion of the screen. This solution, in tests which dissociate between right and left eye, halves the portion of the screen seen by each eye and makes overlapping of stimuli impossible. Moreover, this methodology does not enable to take into account the correct convergence between the eyes, invalidating the quality and correctness of the examination, especially in tests with three-dimensional images, in which the slight deviation of the two eyes allows fusion of images into one vision, providing the perception of depth and of stereoscopic sight. According to a further methodology of the known art, differently coloured filters are used for each eye. In healthy subjects, a high degree of dissociation between the two eyes can be achieved, and stimuli can overlap, but these stimuli are chromatically altered, and in case of chromatic imbalance (for example colour blindness) this cannot lead to reliable results. Moreover, this methodology proves completely useless in three-dimensional tests because, as previously stated, these tests aim at showing each eye the same image, perceived from two different points of view without inducing any chromatic alteration between the two visions. In another technical field, and precisely in the field of cinematic vision, a very complex and expensive system was developed (commonly called by the name of the commercial product I-MAX), which entails the alternate projection of two image flows. The viewer wears special goggles, which are synchronized with the two projectors and alternately dim the two lenses so that the viewer's right eye always perceives the images projected by projector number one, and similarly, the left eye always perceives the images projected by projector number two. These images represent the same object, yet seen from two conveniently different points; moreover, the frequency of commutation of the lenses, and hence of the projectors, is high enough to prevent the eye from detecting the same commutation.

SUMMARY OF THE INVENTION

Therefore, the aim of this invention is to sort out all the above inconveniences and to provide a method to represent images for dissociative stereoscopic vision, which enables to make use of the whole screen portion for each eye, without having to deal with problems deriving from the use of chromatic filters. Another aim is to enable overlapping of stimuli directed to both eyes on the same screen. This invention is also aimed at providing a method which allows to use reasonably priced electronic devices. A further aim of this invention is to provide an example of preferred realisation of a system suitable to perform this method. This invention is hence focused on a method to represent images for dissociative stereoscopic vision and related system, as better described in the claims, which are an integral part of this description. Further aims and benefits of this invention will result clear from the following detailed description of a preferred embodiment of the invention (and of its variants) as well as from the annexed drawings, which include but are not limited to the following:

BRIEF DESCRIPTION OF THE DRAWINGS

The same numbers and the same reference letters in the figures identify the same elements or components.

DETAILED DESCRIPTION OF THE INVENTION

Figure 1:
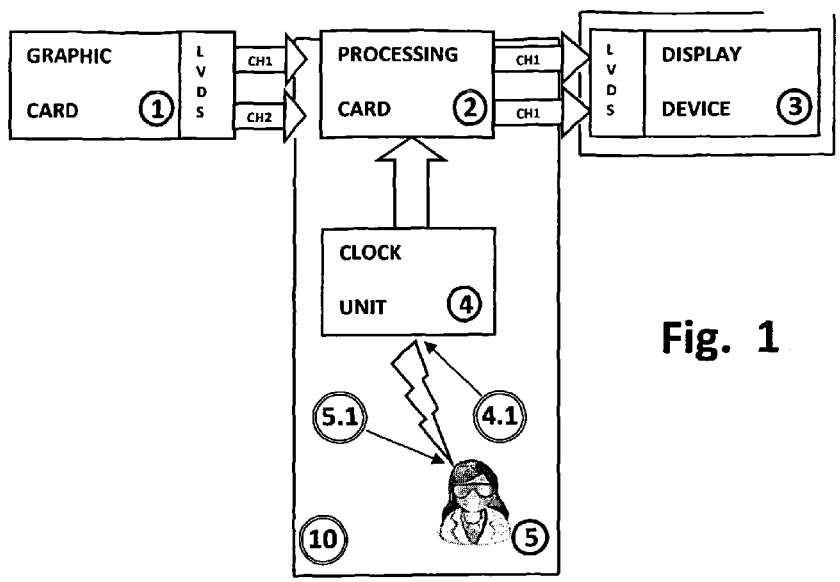
FIG. 1 features a broad block diagram of the system, which implements the method of this finding. The clock block 4 is highlighted, it commands switching of images and shuttering of goggle lenses 5.

This finding features a method entailing the following stages:
1. fetching the right and left images for stereoscopic vision;
2. suppressing even columns for one of the two images and odd columns for the other image;
3. merging images derived from step 2 in order to create one single image made up of the alternating columns belonging to the two images, so that the odd columns precisely belong to the first image and the even columns precisely belong to the second image;
4. splitting the image obtained in the above step into the two images obtained in step 2;
5. filling the generic empty column i with the data contained in column i+1, or as an alternative with the data contained in column i−1, for both images obtained in step 4;
6. alternately showing the two images obtained in step 5, on a video at high frequency, synchronously blanking the right and left lenses worn by the patient, so that the right eye always sees image number one, and the left eye always sees image number two (or vice versa).

Profitably, this solution allows to input to a graphic card 1 of a normal computer, an image obtained in step 3 of the previous method, which equipped with LVDS (Low Voltage Differential Signalling) output, features as output the even and odd columns, in two different channels, de facto performing step 4 of the previous method. The above columns in step 2 have a pixel amplitude in line with the LVDS video flows which is the output from graphic card 1.

Profitably, no workload is loaded to the graphic card, which will only deliver a static image as an output, and this static image is the result of off-line processing, according to method steps 1 and 2.

System 10, the focus of this invention, is depicted in line with the block diagram and is made up of:
1. clock unit 4, which spells out the synchronization time between the image processor 2 and the goggles 5 worn by the patient, equipped with a communication system 4.1 to deliver the timing data to the goggles;

2. image processing card 2, which at each clock event, in line with method steps 5 and 6, shows a video 3 alternating one of the two images obtained by duplicating the missing columns, starting from the adjacent previous or next one.

3. a pair of goggles 5 with liquid crystal lenses equipped with a communication system 5.1 and with an high-frequency circuitry to alternately shut the lenses.

Profitably, the above device is nothing but a box equipped with LVDS input (from graphic card 1), LVDS output (towards a generic display system), and power wire. It is therefore extremely easy to set up and use during medical examinations. The above communication system 4.1 is compatible with the above communication system 5.1 and can be used both with wired and wireless transmission, ie. with infrared or Bluetooth or WIFE transmission. The image projected from a video projector, where no goggles are used, is seen as two different things overlapping, mixed-up and unrecognizable. By using electronic goggles 5, which can alternately block the sight of the right eye and of the left eye, in line with the signal emitted by clock unit 4, the patient will be able to perceive the first image only with the first eye and the second one only with the second eye.

It is therefore clear that the method on which this invention is based and the deriving device will allow using a common and economical computer equipped with a common graphic card 1 equipped with LVDS output and a generic display system. Between these the device is inserted, which coupled with goggles 5 will perform method steps 5 and 6.

It goes without saying that the first three method steps can be performed off-line by means of a suitable software. When the above processing card 2 is disabled, the signal of the 2 LVDS channels is transferred without any output changes. In this case display of the display device 3 is absolutely standard and the card behaves like a channel without any action.

Figure 2:
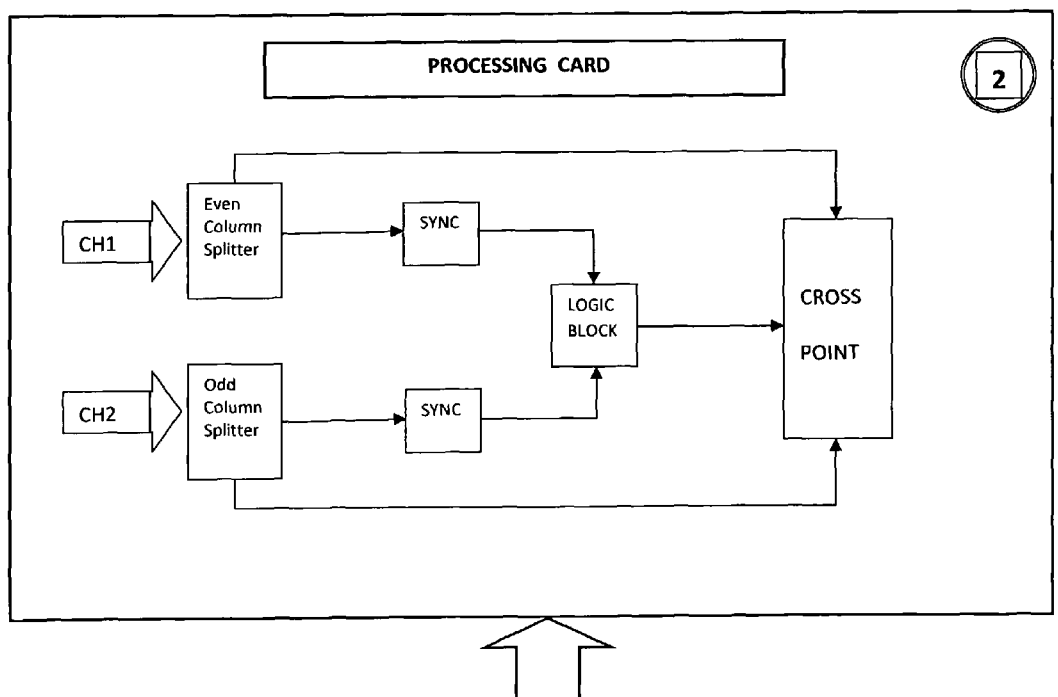
FIG. 2 features the block diagram of the image processing card 2.

The above card can be enabled to partial operation, that is enabling the output of one of the two video input flows, also allowing tests for one single eye. In the above preferred realisation of the processing card (see FIG. 2) splitters are simple high-frequency signal splitters. One of the outputs is used to obtain video synchronism signals contained and encoded together with the data, while the other output goes to the Cross Point, namely a switch which can either block or let an input signal through towards the output and link the input channel to one of the output channels both in straight and exchanged connection. Through the control signals originating from the computer and the signals originating from clock unit 4, the control logic (logic block) enables and controls the functionality of the Cross Point and therefore of the even or odd rows or both. In the block diagram, the "Control Signals" are related to the commands of the management program transmitted from the main PC to the microcomputer of the processing card 2 by means of dedicated Input/Output lines.

This invention can be opportunely implemented using a computer program that includes means of encryption to implement the first three steps of the method, when this program is run on a computer. Therefore it is understood that the scope of protection extends to said program and also to computer readable means that include a recorded message. Said computer readable means shall include means to encrypt a program used to perform one or more method steps, when said program is run on a computer.

Variants of this non-limitative example are possible, within the scope of protection of this invention, including all equivalent implementations for a specialized technician. By reading the above description, a specialized technician will be able to implement the object of the invention without introducing any further construction details.

The invention claimed is:

1. A method to represent images for dissociative stereoscopic vision, comprising the following steps:
   a. fetching right and left images for stereoscopic vision;
   b. suppressing even columns for one of the two images and odd columns for the other image;
   c. fusing images derived from step b in order to create one single image made up of alternating columns belonging to the two images, so that the odd columns precisely belong to the first image and the even columns precisely belong to the second image;
   d. splitting the image obtained step c into the two images obtained in step b;
   e. filling a generic empty column i with data contained in column i+1, or as an alternative with data contained in column i−1, for both images obtained in step d;
   f. alternately showing the two images obtained in step e, on a video at high frequency, synchronously blanking right and left lenses worn by a patient, so that a right eye always sees a first image, and a left eye always sees a second image, or vice versa.

2. An image representation system for dissociative stereoscopic vision suitable to perform the method of claim 1, comprising the following features:
   a clock unit, which spells out a synchronization time between an image processor and goggles worn by the patient, said clock unit equipped with a communication system to deliver timing data to the goggles;
   an image processing card, which at each clock event, in line with steps e and f of the method of claim 1, shows a video alternating one of the two images obtained by duplicating the missing columns, starting from the adjacent previous or next one; and,
   a pair of goggles with liquid crystal lenses equipped with a communication system, and with an alternate high-frequency shutter system for the lenses.

3. The method of claim 1, wherein each of the steps a, b and c is run on a computer having a computer program which includes encryption means to implement the steps a, b, and c.

4. The method of claim 1, wherein each of the steps a, b and c is run on a computer having a computer readable means which includes a recorded message and a computer program which includes encryption means to perform the steps a, b, and c.

* * * * *